(12) United States Patent
Trummer-Sailer

(10) Patent No.: US 9,735,391 B2
(45) Date of Patent: Aug. 15, 2017

(54) ORGANIC OPTOELECTRONIC COMPONENT

(71) Applicant: OSRAM OLED GmbH, Regensburg (DE)

(72) Inventor: Evelyn Trummer-Sailer, Mintraching (DE)

(73) Assignee: OSRAM OLED GmbH, Regensburg (DE)

( * ) Notice: Subject to any disclaimer, the term of this patent is extended or adjusted under 35 U.S.C. 154(b) by 0 days.

(21) Appl. No.: 14/785,733

(22) PCT Filed: May 12, 2014

(86) PCT No.: PCT/EP2014/059641
§ 371 (c)(1),
(2) Date: Oct. 20, 2015

(87) PCT Pub. No.: WO2014/184135
PCT Pub. Date: Nov. 20, 2014

(65) Prior Publication Data
US 2016/0072097 A1    Mar. 10, 2016

(30) Foreign Application Priority Data
May 15, 2013   (DE) ................. 10 2013 105 003

(51) Int. Cl.
*H01L 51/52* (2006.01)
*H01L 51/00* (2006.01)
(Continued)

(52) U.S. Cl.
CPC ....... *H01L 51/5253* (2013.01); *G01N 27/041* (2013.01); *H01L 51/0031* (2013.01);
(Continued)

(58) Field of Classification Search
CPC .... H01L 51/56; H01L 51/524; H01L 51/5253
See application file for complete search history.

(56) References Cited

U.S. PATENT DOCUMENTS

2005/0025881 A1   2/2005  Daniels
2008/0237872 A1  10/2008  Nagayama
(Continued)

FOREIGN PATENT DOCUMENTS

CN     102386210 A      3/2012
JP    2008192326 A  *   8/2008
(Continued)

*Primary Examiner* — Kyoung Lee
*Assistant Examiner* — Christina Sylvia
(74) *Attorney, Agent, or Firm* — Slater Matsil, LLP

(57) ABSTRACT

An organic optoelectronic component includes a first electrode which is made of an electrically conductive material, an active region which is made of an organic material, a second electrode which is made of an electrically conductive material, an encapsulating layer sequence which is made of a dielectric material, and a third electrode which is made of an electrically conductive material. The first electrode and the second electrode are arranged on different sides of the active region. The encapsulating layer sequence is arranged between the first electrode and the third electrode. The first electrode, the second electrode, and the third electrode can be contacted from outside the component.

15 Claims, 3 Drawing Sheets

(51) Int. Cl.
  *G01N 27/04*   (2006.01)
  *H01L 51/44*   (2006.01)
  *H01L 51/56*   (2006.01)

(52) U.S. Cl.
  CPC .......... *H01L 51/441* (2013.01); *H01L 51/448* (2013.01); *H01L 51/5206* (2013.01); *H01L 51/5221* (2013.01); *H01L 51/56* (2013.01); *H01L 2251/301* (2013.01)

(56) References Cited

U.S. PATENT DOCUMENTS

| | | | |
|---|---|---|---|
| 2011/0049730 A1 | 3/2011 | Schmid et al. | |
| 2012/0326175 A1* | 12/2012 | Hu | H01L 33/46 257/88 |
| 2014/0084315 A1* | 3/2014 | Huang | H01L 24/97 257/91 |

FOREIGN PATENT DOCUMENTS

| | | | |
|---|---|---|---|
| JP | 2009277549 A | 11/2009 | |
| WO | 2005051525 A1 | 6/2005 | |

\* cited by examiner

ORGANIC OPTOELECTRONIC COMPONENT

This patent application is a national phase filing under section 371 of PCT/EP2014/059641, filed May 12, 2014, which claims the priority of German patent application 10 2013 105 003.4, filed May 15, 2013, each of which is incorporated herein by reference in its entirety.

TECHNICAL FIELD

An organic optoelectronic component is provided. A method for determining the quality of an encapsulation layer sequence in an organic optoelectronic component is furthermore provided.

SUMMARY

Embodiments of the invention provide an organic optoelectronic component in which quality control may be particularly simply and economically carried out.

The organic optoelectronic component described herein may, for example, be a radiation-generating component such as, for example, an organic light-emitting diode (OLED). It is furthermore possible for the component to form an organic photodiode or an organic solar cell.

According to at least one embodiment of the organic optoelectronic component, the component comprises a first electrode which is formed with an electrically conductive material.

The first electrode and also the further electrodes described below may, for example, be formed with a metal and/or with a metal oxide. The electrodes may be radiation-transmissive or radiation-reflective.

A radiation-transmissive electrode described herein is, for example, transmissive to at least 50%, in particular to at least 80% of the electromagnetic radiation generated or received in the component and impinging thereon during operation. A radiation-transmissive electrode may here be radiation-scattering or transparent and clear.

A radiation-reflective electrode described herein is, for example, reflective to at least 50%, in particular to at least 80%, of the electromagnetic radiation generated or received in the component and impinging thereon during operation. A radiation-reflective electrode may here be diffusely or directionally reflective.

The first electrode may be a radiation-reflective or radiation-transmissive electrode.

According to at least one embodiment of the organic optoelectronic component, the component comprises an active region which is formed with an organic material. Depending on the nature of the component, electromagnetic radiation, in particular light, is generated or received when the component is in operation.

According to at least one embodiment of the organic optoelectronic component, the component comprises a second electrode which is formed with an electrically conductive material. The second electrode may be a radiation-reflective or radiation-transmissive electrode.

According to at least one embodiment of the organic optoelectronic component the organic optoelectronic component comprises an encapsulation layer sequence which is formed with a dielectric material. The encapsulation layer sequence comprises at least one layer, preferably at least two or a plurality of layers, which is/are formed with a dielectric material. Different layers of the encapsulation layer sequence may here comprise materials which differ from one another.

The encapsulation layer sequence is provided to protect the organic material of the active region from moisture and/or atmospheric gases. For example, the encapsulation layer sequence prevents moisture and/or atmospheric gases from passing through. The encapsulation layer sequence may cover the active region at all free outer surfaces of the active region.

For example, the encapsulation layer sequence is applied onto the outer surface of the active region by deposition or vacuum evaporation. For example, the encapsulation layer sequence may be produced by methods such as CVD and/or ALD. The encapsulation layer sequence may here contain materials such as SiN, $SiO_2$, AN or $Al_2O_3$. Further materials and production methods for producing an encapsulation layer sequence are described, for example, in U.S. Patent Application Publication No. 2011/0049730, which is hereby included by reference.

The material of the encapsulation layer sequence is preferably a dielectric, i.e., an electrically weakly conductive or nonconductive, nonmetallic substance. The encapsulation layer sequence acts, at least when intact, as an electrical insulator.

According to at least one embodiment of the organic optoelectronic component, the component comprises a third electrode which is formed with an electrically conductive material. The third electrode may, for example, be a radiation-transmissive or a radiation-reflective electrode. When the component is in operation, the third electrode is not intended for current feed and is not energized. In particular, the region between the encapsulation layer sequence and the further electrodes, i.e., for example, the third, fourth and fifth electrodes, is free of functional components which are operated electrically. The further electrodes thus then do not serve to operate elements of the component.

According to at least one embodiment of the organic optoelectronic component, the first electrode and the second electrode are arranged on different sides of the active region. For example, the two electrodes at least partially, in particular completely, cover two mutually opposing major faces of the active region. The first and the second electrode are provided for energizing the active region or carrying charge carriers away from the active region. The first and the second electrode are in each case electrically conductively connected with the active region and, via the active region, with one another. The first and the second electrode thus serve to connect the active region electrically.

According to at least one embodiment of the organic optoelectronic component, the encapsulation layer sequence is arranged between the first electrode and the third electrode. For example, the first electrode and the third electrode are arranged on different mutually opposing major faces of the encapsulation layer sequence. The encapsulation layer sequence electrically insulates, at least when intact, the first electrode from the third electrode. The third electrode does not serve for electrical connection of the active region nor for electrical connection of a further component. If the encapsulation layer sequence is intact, the third electrode is electrically insulated from the active region by the encapsulation layer sequence.

According to at least one embodiment of the organic optoelectronic component, the first electrode, the second electrode and the third electrode are contactable from outside the component. In other words, for each of the three electrodes there is a contact present via which the electrode is electrically contactable. The active region of the component may be operated via the electrical contact which is assigned to the first electrode and the electrical contact which is assigned to the second electrode.

According to at least one embodiment provides the organic optoelectronic component. A first electrode is formed with an electrically conductive material. An active region is formed with an organic material. A second electrode is formed with an electrically conductive material. An encapsulation layer sequence is formed with a dielectric material. A third electrode is formed with an electrically conductive material. The first electrode and the second electrode are arranged on different sides of the active region. The encapsulation layer sequence is arranged between the first electrode and the third electrode. The first electrode, the second electrode and the third electrode are contactable from outside the component.

According to at least one embodiment of the component, a component is provided in which an encapsulation layer sequence is arranged between two electrodes, for example, the first electrode and the third electrode. The encapsulation layer sequence is formed with a dielectric material and, when intact, insulates these two electrodes electrically from one another.

A method for determining the quality of an encapsulation layer sequence in an organic optoelectronic component is further provided. A component is provided for the method, in which component an encapsulation layer sequence, which is, for example, formed with a dielectric material, is arranged in particular directly between two electrodes. An electrical voltage is applied between the two electrodes. On the basis of measurements of electrical properties of the encapsulation layer sequence, it is possible to make statements regarding the integrity and hence the quality of the encapsulation layer sequence. For example, the permittivity and/or electrical resistance of the encapsulation layer sequence are determined in the method.

The component and the method which are described here are based inter alia on the insight that, by applying the third electrode over the encapsulation layer sequence, it is possible to test the integrity of the encapsulation layer sequence and hence the quality of encapsulation of the component. For example, a voltage may be applied between the first electrode and the third electrode which in each case adjoin the encapsulation layer sequence. As a consequence, it is, for example, possible to carry out non-destructive testing of the dielectric properties, such as permittivity and/or electrical resistance, of the encapsulation layer sequence. In this way, it is possible to measure the integrity of the encapsulation layer sequence and to identify poorly encapsulated components. In so doing, it is possible to identify not only poor encapsulation arising due to impressed particles during application of a cover onto the encapsulation layer sequence but also poor encapsulation resulting from a production process which was not error-free.

Poor encapsulation due to defective production may, for example, be identified because the permittivity of the encapsulation layer sequence is below a nominal value, which may, for example, indicate entrapped air in the encapsulation layer sequence. Furthermore, "pinholes" may be indicated by an electrical resistance which is below a nominal value. Inclusions of foreign particles in the encapsulation layer sequence may also be identified by a deviation in permittivity and/or electrical resistance from a nominal value.

The method may, for example, be carried out on a component described herein. In other words, all the features disclosed for the component are also disclosed for the method and vice versa.

It has further been found that, in addition to its use for testing the quality of the encapsulation layer sequence, the third electrode may provide further advantages. For example, depending on the material and thickness, the third electrode may provide protection against particles which may be impressed in further process steps. The third electrode may furthermore have an encapsulation effect and hence further improve encapsulation of the component. The third electrode may furthermore reduce mechanical strain (for example, layer stress) in the component.

According to at least one embodiment of the organic optoelectronic component, the encapsulation layer sequence directly adjoins the first electrode and the third electrode. In other words, the encapsulation layer sequence and the adjoining electrodes have common cross-sectional areas over which they are in direct contact with one another. For example, the first electrode and the third electrode may completely cover mutually opposing major faces of the encapsulation layer sequence and in places project beyond a lateral direction, i.e., a direction parallel to the main plane of extension of the encapsulation layer sequence.

According to at least one embodiment of the organic optoelectronic component, the first electrode and the second electrode are electrically conductively connected to the active region and the third electrode is electrically insulated from the active region by the encapsulation layer sequence. The second electrode is, for example, on a bottom of the active region. The first electrode may then be arranged on the top, remote from the second electrode, of the active region. The encapsulation layer sequence may then be arranged on the top, remote from the active region, of the first electrode. The third electrode is then arranged on the top, remote from the first electrode, of the encapsulation layer sequence.

According to at least one embodiment of the organic optoelectronic component, the first electrode and the second electrode are electrically insulated from the third electrode by the encapsulation layer sequence. The first and second electrode may here be electrically conductively connected to one another by the active region.

According to at least one embodiment of the organic optoelectronic component, the component comprises at least one further encapsulation layer sequence and at least one further, for example, fourth, electrode. The further encapsulation layer sequence is here arranged between the further electrode and another electrode of the component. The quality, in particular the integrity, of the further encapsulation layer sequence may be determined by means of the further electrode and the other electrode of the component by applying a voltage to the two electrodes. The further electrodes do not, however, serve to operate a element of the component, such that, for example, no current feed proceeds when the component is in operation.

The component may comprise a plurality of encapsulation layer sequences, wherein a pair of electrodes is preferably assigned to each encapsulation layer, by means of which pair of electrodes the quality of the encapsulation layer sequence may be tested using a method described herein. To this end, each of the electrodes is electrically connectable from outside the component.

According to at least one embodiment of the organic optoelectronic component, the component comprises a fourth electrode which is formed with an electrically conductive material and a further encapsulation layer sequence which is with a dielectric material. It is here in particular possible for the further encapsulation layer sequence to be arranged directly between the third electrode and the fourth electrode or directly between the second electrode and the fourth electrode. The quality of the further encapsulation layer sequence may be determined using the method described herein by means of the electrodes, between which the further encapsulation layer sequence is arranged.

According to at least one embodiment of the organic optoelectronic component, the third electrode is transmissive to electromagnetic radiation generated or received in the active region when the component is in operation. In other words, electromagnetic radiation generated in the component leaves the component at least in part through the encapsulation layer sequence and the third electrode.

According to at least one embodiment of the organic optoelectronic component, the third electrode projects beyond the active region in the lateral direction. In this way, the third electrode may be particularly straightforwardly contacted from outside the component, because it is freely accessible at a lateral distance from the active region.

According to at least one embodiment of the organic optoelectronic component, a covering body transmissive to the electromagnetic radiation generated or received in the active region when the component is in operation is arranged on a side, remote from the active region, of the third electrode. The covering body here provides mechanical protection for the underlying layers of the component. For example, the covering body is adhesively bonded or laminated onto the top, remote from the encapsulation layer sequence, of the third electrode. The third electrode may here provide mechanical protection for the encapsulation layer sequence from particles which, in the absence of the third electrode, are impressed into the encapsulation layer sequence and so reduce the quality thereof during application of the covering body. Before and after application of the covering body, the quality of the encapsulation layer sequence may be tested using the method described herein. In this way, by comparing the measurements before and after application, it is possible to identify whether the encapsulation layer sequence has suffered damage due to application of the covering body.

All in all, it is possible for the method described herein to be carried out a number of times on the same component. For example, the method is carried out after specific processing steps, such as, for example, application of the covering body, and before said processing steps. A comparison of the measurements obtained during the method, for example, for the permittivity or electrical resistance of the measured encapsulation layer sequence, may provide information as to whether the encapsulation layer sequence has suffered damage during the processing step. During development of the components described herein, the method may also be used to obtain information as to which processing steps are particularly critical with regard to damaging the encapsulation.

The covering body described herein may, for example, be a glass sheet, a metal foil, a graphite film or a plastics film. The covering body may be attached by lamination or adhesive bonding.

BRIEF DESCRIPTION OF THE DRAWINGS

The component described herein and the method described herein are explained in greater detail below with reference to exemplary embodiments and the associated figures.

Figure 1:
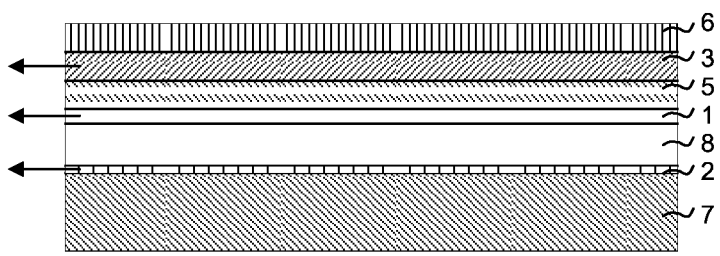
FIGS. 1, 2, 3 and 4 show schematic sectional views of exemplary embodiments of components described herein.

Identical, similar or identically acting elements are provided with identical reference numerals in the figures. The figures and the size ratios of the elements illustrated in the figures relative to one another are not to be regarded as being to scale. Rather, individual elements may be illustrated on an exaggeratedly large scale for greater ease of depiction and/or better comprehension.

DETAILED DESCRIPTION OF ILLUSTRATIVE EMBODIMENTS

A first exemplary embodiment of a component described herein is explained in greater detail in FIG. 1 with reference to a schematic sectional view. The component comprises a carrier 7. The carrier 7 is, for example, formed with a metal, a plastic and/or a glass.

The second electrode 2 is arranged on the top of the carrier 7. In the present case, the second electrode 2 is, for example, an anode. The second electrode 2 may in the present case be radiation-reflective.

The active region 8 which is formed with an organic material is arranged on the top, remote from the carrier 7, of the second electrode 2. The component shown is, for example, an organic light-emitting diode, in which, during operation thereof, light is generated in the active region 8.

The first electrode 1, which in the present case is, for example, radiation-transmissive, is arranged on the top, remote from the second electrode 2, of the active region 8. The first electrode 1 is, for example, a cathode of the component.

The encapsulation layer sequence 5, which in the present case is a thin-film encapsulation, is arranged on the top, remote from the active region 8, of the first electrode 1.

The third electrode 3 is then arranged on the top, remote from the first electrode 1, of the encapsulation layer sequence 5.

All of electrodes 1, 2 and 3 are electrically contactable from outside the component, this being indicated by arrows in FIG. 1. The third electrode 3 forms neither an anode nor a cathode of the component and does not serve for electrically connecting or for operating the active region 8.

A method described herein may be carried out on the component of the exemplary embodiment of FIG. 1 by applying a voltage to the first electrode 1 and the third electrode 3. As a consequence, it is, for example, possible to carry out non-destructive testing of the dielectric properties, such as permittivity and/or electrical resistance, of the encapsulation layer sequence 5. In this way, it is possible to measure the integrity of the encapsulation layer sequence 5 and to identify poorly encapsulated components. In so doing, it is possible to identify not only poor encapsulation arising due to impressed particles during application of a covering body 6 onto the encapsulation layer sequence 5 but also poor encapsulation resulting from a production process which was not error-free. This is based on the recognition that the dielectric properties of the encapsulation layer sequence 5 are prevented by defects such as, for example, pinholes and impressed particles.

The third electrode 3 may here assume still further functional tasks in the component. For example, the third electrode 3 provides mechanical protection for the underlying layers and/or forms a further encapsulation in particular of the organic material of the active region 8 against moisture and/or atmospheric gases.

The covering body 6 is here, for example, a laminated piece of glass or an adhesively bonded film and is arranged on the top, remote from the encapsulation layer sequence 5, of the third electrode 3.

Figure 2:
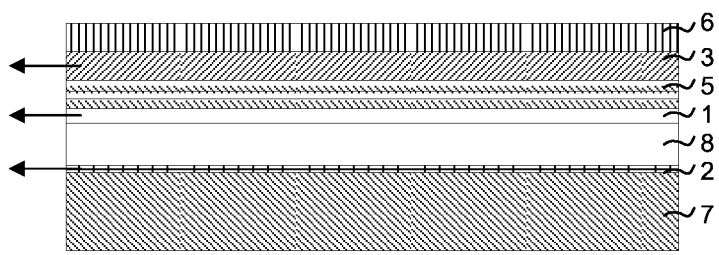
Figure 3:
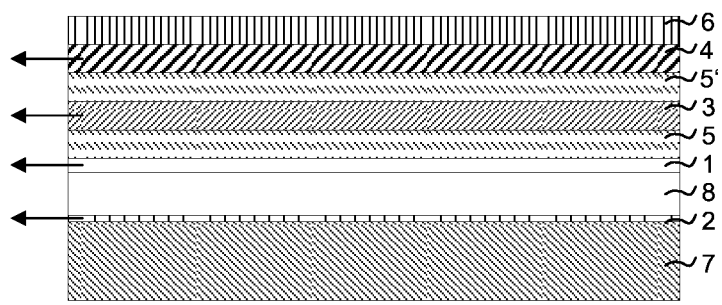

A further exemplary embodiment of a component described herein is explained in conjunction with the schematic sectional representation of FIG. 2. In contrast with the component of FIG. 1, the encapsulation layer sequence 5 in this exemplary embodiment is formed from two or more layers. Different layers of the encapsulation layer sequence may here consist of different materials and/or be produced by different methods. In contrast with the component which is described in conjunction with FIG. 1, the component which is described in conjunction with FIG. 3 comprises a further encapsulation layer sequence 5' which is arranged on the top, remote from the encapsulation layer sequence 5, of the third electrode 3. The component additionally comprises a fourth electrode 4 which is arranged on the top, remote from the further encapsulation layer sequence 5', of the third electrode 3.

It has been found that the measurements on the encapsulation layer sequence 5 become more inaccurate as the layer thicknesses of the encapsulation layer sequence 5 increase. In the exemplary embodiment of FIG. 3, this problem is solved in that a plurality of encapsulation layer sequences 5 are present, wherein a further electrode is assigned to each further encapsulation layer sequence. The further layers may additionally assume further tasks. Depending on the selected material, they make a contribution to the encapsulation effect, to reducing mechanical strains, to providing protection from impressed particle and/or to mechanically protecting the component.

Figure 4:
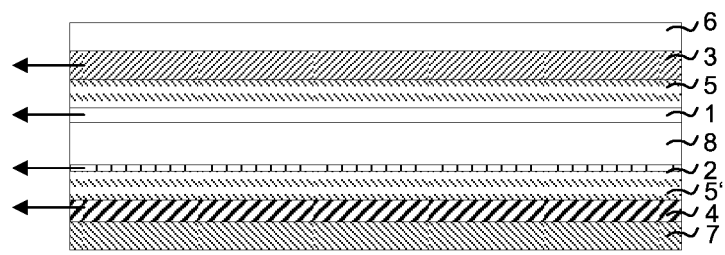

In the component of FIG. 4, the further encapsulation layer sequence 5' is arranged below the first electrode 1. The fourth electrode 4 is here arranged between the carrier 7 and the further encapsulation layer sequence 5'. This has in particular proved advantageous for top-emitters or components which emit from both sides.

Figure 5:
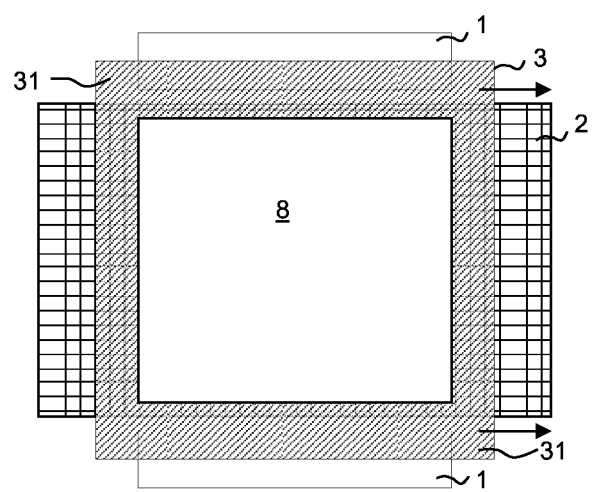
FIGS. 5, 6 and 7 show schematic plan views of components described herein.
Figure 6:
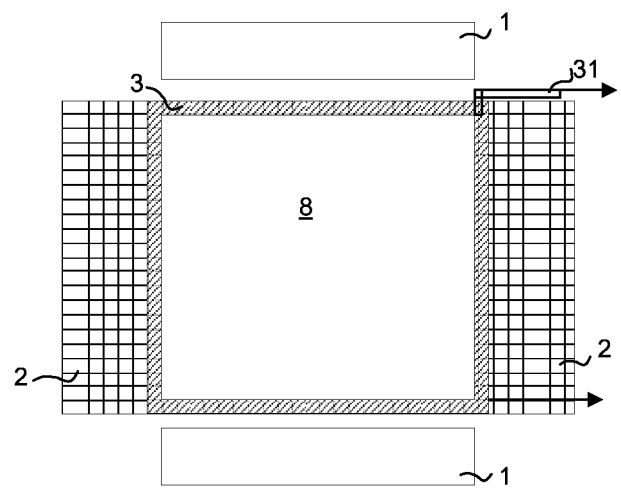
Figure 7:
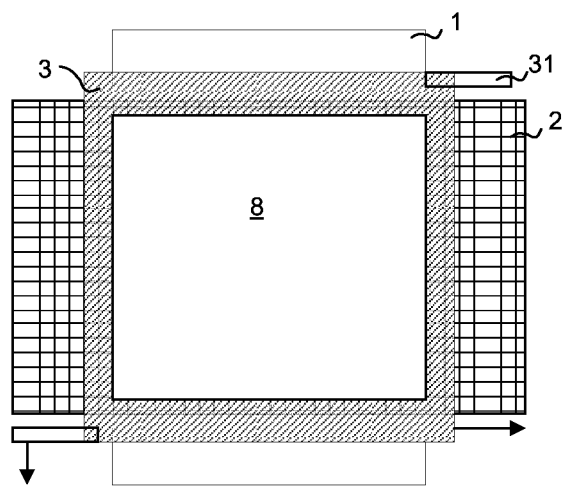

FIGS. 5, 6 and 7 explain the contacting of the electrodes of a component described herein in greater detail.

FIG. 5 shows a further exemplary embodiment of a component described herein with reference to a schematic plan view.

In the exemplary embodiment of FIG. 5, the third electrode 3 is constructed such that it projects beyond the active region 8 in a lateral direction. In this way, contact regions 31 for contacting the third electrode 3 are obtained. In the exemplary embodiment of FIG. 5, the encapsulation layer sequence 5 is likewise of a large area, such that it projects beyond the active region 8 in the lateral direction in the same way as the third electrode 3. In this way, it is possible for the third electrode 3 to overlap with the other two further electrodes 1 and 2 of the component.

In conjunction with FIG. 6, an exemplary embodiment is shown in which the encapsulation layer sequence 5 does not extend over the entire surface, but instead only covers the active region 8. In the exemplary embodiment of FIG. 6, contact regions 31 in the form of contact webs are guided outwards from the third electrode 3 in order to avoid short-circuiting with the other two further electrodes 1 and 2 of the component.

In conjunction with FIG. 7, a combination of the exemplary embodiments of FIGS. 5 and 6 is explained.

The description made with reference to exemplary embodiments does not restrict the invention to these embodiments. Rather, the invention encompasses any novel feature and any combination of features, including in particular any combination of features in the claims, even if this feature or this combination is not itself explicitly indicated in the claims or exemplary embodiments.

The invention claimed is:

1. An organic optoelectronic component comprising:
   a first electrode comprising an electrically conductive material;
   an active region comprising an organic material;
   a second electrode comprising an electrically conductive material, wherein the first electrode and the second electrode are arranged on different sides of the active region;
   a third electrode comprising an electrically conductive material, wherein the first electrode, the second electrode and the third electrode are contactable from outside the component; and
   an encapsulation layer sequence comprising a dielectric material, wherein the encapsulation layer sequence is arranged between the first electrode and the third electrode, and
   wherein the third electrode is not provided for current feed when the component is in operation.

2. The organic optoelectronic component according to claim 1, wherein the third electrode is not provided for operating an element of the component.

3. The organic optoelectronic component according to claim 1, wherein the encapsulation layer sequence directly adjoins the first electrode and the third electrode.

4. The organic optoelectronic component according to claim 1, wherein the first electrode and the second electrode are electrically conductively connected to the active region and the third electrode is electrically insulated from the active region by the encapsulation layer sequence.

5. The organic optoelectronic component according to claim 1, wherein the first electrode and the second electrode are electrically insulated from the third electrode by the encapsulation layer sequence.

6. The organic optoelectronic component according to claim 1, further comprising:
   a fourth electrode formed with an electrically conductive material; and
   a further encapsulation layer sequence formed with a dielectric material, wherein the further encapsulation layer sequence is arranged directly between the third electrode and the fourth electrode.

7. The organic optoelectronic component according to claim 1, further comprising:
   a fourth electrode formed with an electrically conductive material; and
   a further encapsulation layer sequence formed with a dielectric material, wherein the further encapsulation layer sequence is arranged directly between the second electrode and the fourth electrode.

8. The organic optoelectronic component according to claim 1, wherein the third electrode is transmissive to electromagnetic radiation generated or received in the active region when the component is in operation.

9. The organic optoelectronic component according to claim 1, wherein the third electrode projects beyond the active region in a lateral direction.

10. The organic optoelectronic component according to claim 1, further comprising a covering body that is transmissive to electromagnetic radiation generated or received in the active region when the component is in operation, wherein the covering body is arranged on a side of the third electrode that is remote from the active region.

11. The organic optoelectronic component according to claim 1, wherein the first electrode and the second electrode are arranged on different sides of the active region, and wherein the first electrode and the second electrode completely cover two mutually opposing major faces of the active region.

12. The organic optoelectronic component according to claim 11, wherein the third electrode projects beyond the active region in all lateral directions.

13. A method for determining quality of an encapsulation layer sequence in an organic optoelectronic component, wherein the encapsulation layer sequence is arranged between two electrodes, the method comprising:
   applying an electrical voltage between the two electrodes;
   determining the quality of the encapsulation layer sequence based upon a result of the applying; and
   determining a permittivity of encapsulation layer sequence.

14. The method according to claim 13, further comprising determining an electrical resistance of the encapsulation layer sequence.

15. An organic optoelectronic component comprising:
   a first electrode comprising an electrically conductive material;
   an active region comprising an organic material;
   a second electrode comprising an electrically conductive material, wherein the first electrode and the second electrode are arranged on different sides of the active region;
   a third electrode comprising an electrically conductive material, wherein the first electrode, the second electrode and the third electrode are contactable from outside the component;
   an encapsulation layer sequence comprising a dielectric material, wherein the encapsulation layer sequence is arranged between the first electrode and the third electrode;
   a fourth electrode formed with an electrically conductive material; and
   a further encapsulation layer sequence formed with a dielectric material, wherein the further encapsulation layer sequence is arranged directly between the third electrode and the fourth electrode or wherein the further encapsulation layer sequence is arranged directly between the second electrode and the fourth electrode.

* * * * *